United States Patent [19]

Feth et al.

[11] Patent Number: 4,499,274
[45] Date of Patent: Feb. 12, 1985

[54] PROCESS FOR PREPARATION OF SUBSTITUTED FORMAMIDINE AND SUBSTITUTED N-IMINOMETHYL PIPERIDINE

[75] Inventors: Georg Feth, Schaffhausen, Switzerland; John E. Mills, Hatfield, Pa.

[73] Assignee: McNeilab, Inc., Fort Washington, Pa.

[21] Appl. No.: 476,443

[22] Filed: Mar. 17, 1983

[51] Int. Cl.³ ............... C07D 211/14; C07C 123/00
[52] U.S. Cl. .................................. 546/229; 564/225
[58] Field of Search ..................... 546/229; 564/225

[56] References Cited

U.S. PATENT DOCUMENTS

| 3,971,647 | 7/1976 | Gaetzi et al. | 564/225 |
| 4,251,655 | 2/1981 | Scott et al. | 546/205 |
| 4,353,830 | 10/1982 | Mark | 260/326.86 |
| 4,448,975 | 5/1984 | Mark | 260/326.85 |

FOREIGN PATENT DOCUMENTS 563109  5/1975  Switzerland .

OTHER PUBLICATIONS

H. Bredereck et al., Angew. Chem. Internat. Edit., vol. 1, (1962) No. 6, pp. 331–332.
A. I. Meyers et al., J. Am. Chem. Soc. (1980), vol. 102, pp. 7125–7126.
A. I. Meyers et al., Tetrahedron Letters, vol. 22, No. 51, pp. 5115–5118 (1981).
Roczniki Chemii Ann. Soc. Chim. Polonorum 45, 103 (1971) pp. 103–105.

*Primary Examiner*—Norma S. Milestone
*Attorney, Agent, or Firm*—David J. Levy

[57] ABSTRACT

An improved process for preparing fenoctimine, which is 4-(diphenylmethyl)-1-[(octylimino)methyl]piperidine by: (1) reacting dimethylformamide with dimethyl sulfate to form a complex; (2) reacting the resultant dimethylformamide/dimethyl sulfate complex with n-octylamine and optionally with dimethylamine; (3) thereafter treating the reaction with aqueous base to form N,N-dimethyl-N'-octyl-formamidine; and (4) reacting said formamidine, without need for further purification, with 4-(diphenylmethyl) piperidine to obtain 4-(diphenylmethyl)-1-[(octylimino)-methyl]piperidine.

16 Claims, No Drawings

PROCESS FOR PREPARATION OF SUBSTITUTED FORMAMIDINE AND SUBSTITUTED N-IMINOMETHYL PIPERIDINE

This invention relates to an improved process for preparation of N,N-dimethyl-N'-octylforonamidine (II) which is then used for the preparation of substituted N-iminomethyl piperidines, particularly fenoctimine (III).

Fenoctimine, an antisecretory drug is the USAN name for 4-(diphenylmethyl)-1-[(octylimino)methyl]-piperidine, which has the structure shown in Formula III below. It is currently being clinically tested while administered in the salt form, i.e., as the sulfate (1:1) hydrate (2:1) salt of fenoctimine. It (and analogs thereof) is disclosed in U.S. Pat. No. 4,251,655 wherein various methods are shown for its preparation (in free base or acid addition salt form), especially in Examples V and X thereof. The methods taught there have various deficiencies which make them less desirable for commercial use, so a new process was required.

A new synthetic sequence to N,N-dimethyl-N'-formamidine and then to 4-(diphenylmethyl)-1-[(octylimino)methyl]-piperidine has been discovered which results in superior yields, greater volume efficiency, and simpler isolation and purification of both the formamidine and synthetic intermediates. This new synthetic sequence is shown in the following reaction scheme (A).

It has been found not essential, but advantageous to add dimethylamine to the reaction of dimethylformamide/dialkyl sulfate complex with n-octylamine. The N,N-dimethyl-N'-octylformamidine obtained when dimethylamine is used is produced in high yield and purity.

The transamination reaction is run on the free base of the N,N-dimethyl-N'-octylformamidine with 4-(diphenylmethyl) piperidine at a temperature high enough to give a reasonable rate of conversion to product.

Among the advantages of the process of the present invention over the prior art processes are the following:

1. The optional addition of dimethylamine in step two greatly facilitates the formation of intermediate amidine II by avoiding undesirable side products. While the use of dimethylamine is not essential, it is preferred.
2. A shorter reaction time is required.
3. Intermediate amidine (II) is pure as it emerges from step two (i.e., it does not require distillation as in the prior art process). This greatly simplifies the work-up and produces immediately pure product in high yield compared to the analogous process without dimethylamine.
4. The new process results in a more readily purified fenoctimine free base final product as compared to the presently used methods, and the overall yield is superior.
5. It is a more simple process than currently used.

REACTION SCHEME A

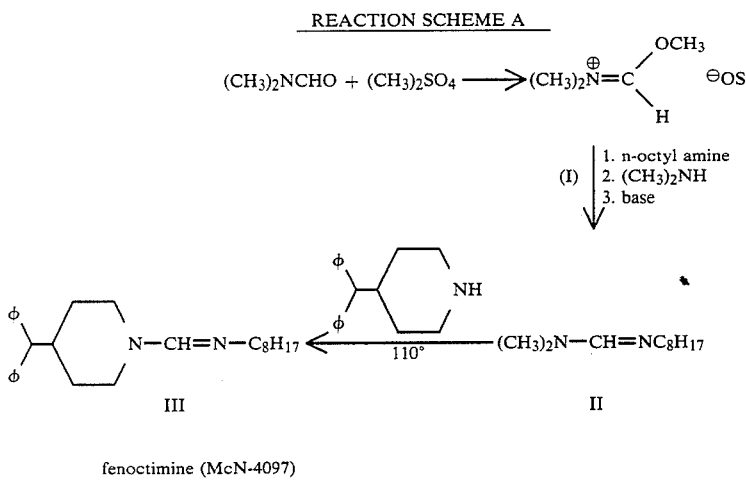

fenoctimine (McN-4097)

PRIOR ART

Amidines have been prepared from the reaction of dimethylformamide with dialkyl sulfate followed by the addition of primary amines [see U.S. Pat. No. 3,971,647; Bredereck and Effenberger, *Angew. Chem. Internat. Edit.*, 1, 331 (1962); and Meyers and Hoeve, *J. Am. Chem. Soc.*, 102, 7125 (1980)]. Formamidines have been shown to react with secondary amines under mild conditions to give transamination products in high yield [see Meyers, Hellring, and Hoeve, *Tetrahedron Letters*, 22, 5115 (1981); and Oszczapowicz and Orlinski, *Roczniki Chemii*, 45, 103 (1971)].

SUMMARY OF THE INVENTION

The sequence of reactions shown in Reaction Scheme A, above, to prepare first N,N-dimethyl-N'-octylformamidine and then 4-(diphenylmethyl)-1-[(octylimino)-methyl]piperidine is novel and forms the basis for the process of the present invention.

PREFERRED EMBODIMENTS

The reaction of dialkyl sulfate with dimethylformamide may be run either with or without additional solvent, as in Examples 2 and 1 respectively, suitable solvents being organic aprotic solvents such as aliphatic halogenated hydrocarbons, aromatic hydrocarbons, and ethereal compounds. On a laboratory scale, it has been found preferable to run the reaction without additional solvent. The molar ratio of dialkyl sulfate to dimethylformamide may be in the range of 1:0.8 to 1:2 or greater. It is preferred that the molar ratio is in the range of 1:1.2 to 1:1.4. The reaction temperature is typically in the range of 50° to 100° C. with a temperature range of 85° to 100° C. being preferred. The reaction time may vary from 1 to 18 hours or longer, with a reaction time of 1 to 3 hours being preferred. The preferred dialkyl sulfate is dimethyl sulfate. Instead of dimethyl sulfate, other reagents such as oxalyl chloride or phosgene could be used to activate the dimethyl formamide. However, the use of dimethyl sulfate offers advantages in terms of cost and ease of handling.

The dimethylformamide/dialkyl sulfate complex can be reacted in situ, without being isolated, with n-octylamine. This reaction may be run either with or without additional solvent, as in Examples 2 or 1 respectively, suitable solvents being organic aprotic solvents such as aliphatic halogenated hydrocarbons, aromatic hydrocarbons, and ethereal compounds. Aromatic hydrocarbons, more specifically toluene, are preferred. The reaction may be run at a temperature between $-30°$ C. and $50°$ C., with a reaction temperature between $0°$ and $25°$ C. being preferred. The molar ratio of n-octylamine to dimethyl sulfate is preferably in the range of 1:1 to 1:1.3. After addition of n-octylamine is complete, the addition to the reaction of dimethylamine in a molar ratio to n-octylamine of 0.1:1 to 0.5:1 has been shown (in Example 3) to give product of higher purity than similar reactions without the dimethylamine (i.e., as in Examples 1 and 2).

The N,N-dimethyl-N'-octylformamidine is isolated by treatment of the reaction with aqueous base followed by work-up through standard procedures. Sodium hydroxide is preferred, but KOH or $Na_2CO_3$, $K_2CO_3$, or any water soluble strong base can be used.

The transamination reaction (Example 4) is run at a temperature of $90°$ C. to $130°$ C. High boiling solvents such as aliphatic hydrocarbons, aromatic hydrocarbons, and ethers may be used, however, no solvent is necessary. An inert gas such as nitrogen or argon may be blown through or over the reaction to aid in the removal of dimethylamine, thereby significantly increasing the yield of end product obtained.

The following are intended to illustrate but not limit the scope of the present invention.

EXAMPLE 1

N,N-Dimethyl-N'-octylformamidine

Dimethyl sulfate (126.1 g, 1.0 mole) was heated to $65°$ C. The temperature was maintained at $60°–70°$ while dimethylformamide (73.1 g, 1.0 mole) was added over a period of about 30 minutes. After the addition was complete, the reaction was heated at $70°$ C. for 7 hours, then cooled to below $30°$ C. n-Octylamine (129.2 g, 1.0 mole) was added over a 20 minute period with external cooling to maintain the temperature at $40°$ C. The reaction was stirred an additional 3 hours at $40°$ C. after addition was complete. The reaction was cooled to about $10°$ C. and treated with toluene (200 ml), water (200 ml) and finally 27% sodium hydroxide solution (180 g 1.2 moles). The organic phase was separated, dried over anhydrous sodium sulfate, filtered and evaporated under reduced pressure to yield 190 g of a light yellow liquid which was fractionally distilled twice to yield 113 g (61%) of the title compound as a water white liquid. b.p. $115°–117°$ C. at 15 mm Hg.

EXAMPLE 2

N,N-Dimethyl-N'-octylformamidine

Dimethylformamide (8.8 g, 0.12 mole), dimethyl sulfate (19.3 g, 0.15 mole) and toluene (20 ml) were placed in a 100 ml round bottom flask and heated at reflux for 30 minutes. During this time a light brown oil separated. The reaction was cooled to room temperature and the toluene was decanted. The dimethylformamide/dimethyl sulfate complex was washed with dry toluene ($2 \times 20$ ml) and the toluene was decanted. n-Octylamine (15.5 g, 0.12 mole) in toluene (20 ml) was added rapidly with stirring. The reaction temperature rose briefly to $60°$ C. The reaction was stirred for 90 minutes, then extracted with a solution of sodium hydroxide (7.2 g, 0.18 mole) in water (40 ml). The organic phase was washed with brine (40 ml), dried over anhydrous $Na_2SO_4$, and filtered. GLC showed the product to be about 72% pure after concentration.

EXAMPLE 3

N,N-Dimethyl-N'-octylformamidine

Dimethyl sulfate (34.7 g, 0.27 mole) was placed in a 300 ml 3-necked round bottom flask equipped with a heating mantle, magnetic stirrer, thermometer, addition funnel and calcium chloride drying tube. The reaction was stirred and warmed to $50°$ C. Heating was discontinued and dimethyl formamide (26 g, 0.36 mole) was added over a 10 minute period. The reaction temperature gradually rose to $85°$ C. The reaction was stirred an additional hour during which time the temperature fell to $45°$ C. The reaction was cooled and maintained between $0°$ and $10°$ C. while n-octylamine (32.3 g, 0.25 mole) in toluene (50 ml) was added over a period of 15 minutes. After the addition was complete, the addition funnel and drying tube were replaced by a dry ice/acetone condenser and gas inlet tube. The cooling bath was removed and gaseous dimethylamine (6.1 g, 0.14 mole) was added over a period of about 5 minutes. The reaction was stirred at room temperature for 1 hour. The reaction was extracted with sodium hydroxide (12.5 g, 0.31 mole) in water (50 ml), washed with brine (25 ml), dried over anhydrous sodium sulfate, filtered and concentrated under reduced pressure to yield 44.5 g (97%) of the title compound as a very light yellow liquid. GLC showed 99.6% of volatiles in a single peak.

EXAMPLE 4

4-(Diphenylmethyl)-1-[(octylimino)methyl]piperidine Sulfate (1:1) Hydrate (2:1), McN-4097-12-98

A. 4-(Diphenylmethyl)piperidine (12.5 g, 0.05 mole) and N,N-dimethyl-N'-octylformamidine (11.5 g, 0.06 mole) were placed in a 3-necked flask equipped with magnetic stirrer, heating mantle, thermometer and nitrogen inlet. A moderate stream of nitrogen was blown through the flask while the reaction was heated to $120°$ C. The reaction was stirred and heated at $120°$ C. for 5 hours, then cooled to $20°$ C. and diluted with toluene (35 ml). The reaction was cooled in an ice bath, stirred, and treated with a mixture of ice (50 g) and sulfuric acid (9 g, 0.088 mole). After stirring for 15 minutes, the resulting solid was isolated by filtration, and washed sequentially with toluene (10 ml), and 1N sulfuric acid ($2 \times 10$ ml). The solid was suspended twice in a mixture of water (100 ml) and 1N sulfuric acid (20 ml) and stirred for 30 minutes each time prior to filtration. Finally, the product was washed with water ($2 \times 10$ ml), and cyclohexane (20 ml). The filter cake was dried under reduced pressure at $30°$ C. to constant weight to yield 21.3 g (85.6%) of the title compound, m.p. $113°–115°$ C.

B. By following the procedure of Example 4A, but substituting a different acid for the sulfuric acid, salts other than the sulfate may be obtained. The free base may be obtained by: (1) distillation of the excess N,N-dimethyl-N'-octylformamidine from the reaction prior to addition of the acid, or (2) by treating a suspension or solution of a salt of 4-(diphenylmethyl)-1-[(octylimino)-methyl]piperidine in a suitable organic solvent with a solution of aqueous base, drying the organic solution over a suitable drying agent, filtration, and concentration under reduced pressure.

We claim:

1. A process for preparing N,N-dimethyl-N'-octylformamidine which comprises the following steps:
    (1) reacting dimethylformamide with dimethyl sulfate to form a dimethylformamide/dimethyl sulfate complex;
    (2) reacting said complex with n-octylamine in the presence of added dimethylamine; and
    (3) thereafter treating the reaction mixture with aqueous base to obtain N,N-dimethyl-N'-octylformamidine.

2. The process of claim 1, wherein in step (2), dimethylamine is added to the reaction mixture after addition of the n-octylamine to the reaction mixture.

3. The process of claim 1, wherein the molar ratio of added dimethylamine to n-octylamine in step (2) is 0.1:1 to 0.5:1.

4. The process of claim 1, wherein in conducting step (1), the molar ratio of dimethyl sulfate to dimethylformamide is from 1:0.8 to 1:2; the reaction temperature is 50°–100° C.; and the reaction time is 1–18 hours.

5. The process of claim 4, wherein said molar ratio of dimethyl sulfate to dimethylformamide is from 1:1.2 to 1:1.4.

6. The process of claim 4, wherein said reaction temperature in step (1) is 85°–100° C.

7. The process of claim 4, wherein in step (1) said reaction time is 1 to 3 hours.

8. The process of claim 1, wherein in step (1) the molar ratio of dimethyl sulfate to dimethylformamide is 1:1.2–1:1.3; the reaction temperature is 50°–85° C.; and the reaction time is 1–2 hours.

9. A process for preparing 4-(diphenylmethyl)-1-[(octylimino)methyl]piperidine which comprises the following steps:
    (1) reacting dimethylformamide with dimethyl sulfate to form a complex;
    (2) reacting the resultant dimethylformamide/dimethyl sulfate complex with n-octylamine in the presence of added dimethylamine;
    (3) thereafter treating the reaction mixture with aqueous base to form, N,N-dimethyl-N'-octylformamidine; and
    (4) reacting said formamidine without further purification with 4-(diphenylmethyl)piperidine, while blowing an inert gas through or over the reaction, to obtain 4-(diphenylmethyl)-1-[(octylimino)methyl]piperidine.

10. The process of claim 9, wherein the molar ratio of added dimethylamine to n-octylamine in step (2) is 0.1:1 to 0.5:1.

11. The process of claim 9, wherein said inert gas is nitrogen.

12. The process of claim 9, wherein said inert gas is argon.

13. The process of claim 9, wherein the temperature in step (4) is 90°–130° C.

14. A process for preparing 4-(diphenylmethyl)-1-[(octylimino)methyl]piperidine which comprises the following steps:
    (1) reacting dimethylformamide with dimethyl sulfate to form a complex;
    (2) reacting the resultant dimethylformamide/dimethyl sulfate complex with n-octylamine in the presence of added dimethylamine;
    (3) thereafter treating the reaction mixture with aqueous base to form N,N-dimethyl-N'-octyl-formamidine; and
    (4) reacting said formamidine with 4-(diphenylmethyl)piperidine to obtain 4-(diphenylmethyl)-1-[(octylimino)methyl]piperidine.

15. The process of claim 14, wherein the molar ratio of added dimethylamine to n-octylamine in step (2) is 0.1:1 to 0.5:1.

16. The process of claim 14, wherein the temperature in step (4) is 90°–130° C.

* * * * *